United States Patent [19]
Wells

[11] Patent Number: 4,844,062
[45] Date of Patent: Jul. 4, 1989

[54] ROTATING FIBEROPTIC LASER CATHETER ASSEMBLY WITH ECCENTRIC LUMEN

[75] Inventor: Lisa D. Wells, Woodland Park, Colo.

[73] Assignee: Spectranetics Corporation, Colorado Springs, Colo.

[21] Appl. No.: 111,645

[22] Filed: Oct. 23, 1987

[51] Int. Cl.[4] .............................................. A61B 17/36
[52] U.S. Cl. ...................................... 128/303.1; 128/6
[58] Field of Search ........................................ 128/4-8, 128/303.1, 395-398; 604/21

[56] References Cited

U.S. PATENT DOCUMENTS

| | | | |
|---|---|---|---|
| 4,256,365 | 3/1981 | Lemesle et al. | 350/96.18 |
| 4,329,017 | 5/1982 | Kapany et al. | 350/96.15 |
| 4,392,485 | 7/1983 | Hiltebrandt | 128/6 |
| 4,545,390 | 10/1985 | Leary | 128/657 |
| 4,576,177 | 3/1986 | Webster | 128/303.1 |
| 4,587,972 | 5/1986 | Morantte | 128/303.1 |
| 4,597,380 | 7/1986 | Raif et al. | 128/303.1 |
| 4,616,631 | 10/1986 | Takahashi | 128/6 |
| 4,627,436 | 12/1986 | Lecksore | 128/305 |
| 4,648,892 | 3/1987 | Kittrell et al. | 64/4.21 |
| 4,693,556 | 9/1987 | McCaughan | 128/303.1 |
| 4,718,417 | 1/1988 | Kittrell et al. | 128/303.1 |

FOREIGN PATENT DOCUMENTS

| | | | |
|---|---|---|---|
| 0005263 | 12/1985 | PCT Int'l Appl. | 128/303.1 |
| 8701273 | 3/1987 | PCT Int'l Appl. | 128/303.1 |

*Primary Examiner*—Max Hindenburg
*Attorney, Agent, or Firm*—Cushman, Darby & Cushman

[57] ABSTRACT

The present invention provides for the ablation of obstructions in vessels such as arteries. A catheter having an optical fiber is used to transmit laser energy to the distal end of the optical fiber. The optical fiber is housed in a lumen within the catheter so that it is eccentric with the catheter and also encompasses the center core of the catheter. A second lumen in the catheter houses a steerable guide wire. The optical fiber is substantially aligned with the distal end of the catheter. This catheter assembly is operated by using the steerable guide wire to advance the catheter assembly to the obstruction, turning the laser on, and then rotating the catheter assembly so that energy from the laser which is emitted from the optical fiber ablates an area which is of a larger diameter than the diameter of the optical fiber. This assembly allows for narrow vessels to be cleared of obstructions with only a minimal chance of perforating the vessel walls.

14 Claims, 2 Drawing Sheets

ROTATING FIBEROPTIC LASER CATHETER ASSEMBLY WITH ECCENTRIC LUMEN

BACKGROUND OF THE INVENTION

1. Field of the Invention

This invention relates to a catheter assembly, and more particularly to a catheter assembly through which an optical fiber passes.

2. Description of Related Art

Fiberoptic catheter assemblies have been increasingly used in clearing obstructions from the pathways of various vessels, such as arteries. The size of the vessels from which the obstruction must be removed determines the size of the catheter which can be placed inside the vessel. Therefore, in certain applications, a catheter with a very small diameter is necessary. However, because of the winding path of various vessels, the catheter must be steerable so that the obstruction can be reached. Once reached, a laser may then provide energy which is transmitted by the optical fiber to ablate the obstruction.

For smaller vessels, a catheter which houses both a guide wire and an optical fiber can be used to advance the catheter assembly to the obstruction in the vessel without causing a perforation of the vessel wall. This has been shown in Anderson, et al.: *Steerable Fiberoptic Catheter Delivery of Laser Energy in Atherosclerotic Rabbits,* Am. Heart J., 111:1065, 1986. The assembly disclosed in the Anderson article shows a catheter with a single lumen which houses both the guide wire and the optical fiber. The hole of the lumen in the Anderson article is also of a large enough diameter to allow for contrast and saline solutions to be injected through the lumen while the optical fiber and guide wire are also running through the lumen. Because of this configuration, the Anderson assembly can only be assured of removing obstructive material from an area directly in front of the tip of the optical fiber. Rotation of the catheter assembly will not necessarily cause the optical fiber to rotate, because the optical fiber and guide wire may simply become twisted within the lumen as the catheter rotates. In fact, the Anderson reference does not even suggest that the catheter assembly be rotated. Even if the fiber rotates, rotation of the catheter assembly will not necessarily result in a maximized ablated area, without leaving a central core of material, since the fiber is not carefully located eccentrically, covering the center of the catheter.

It is also known that fibers with polished, flat-tipped distal ends can easily perforate vessel walls. Sapphire contact probes and quartz shield-tipped catheters have been developed which utilize round, smooth-tipped configurations. This configuration reduces the risk of perforations to the vessel wall by the optical fiber. However, the sapphire contact probes and the quartz shield-tipped catheters currently available have the drawback of having a diameter which is too large to be used in smaller vessels, such as coronary arteries. These devices also require the coupling of a separate tip to the fiber. This coupling causes a greater loss in energy which can be delivered to the obstruction.

A catheter which uses emitted laser energy and is capable of being rotated is also disclosed in U.S. Pat. No. 4,627,436 by Leckrone. For operation, the device must pass the obstruction so that laser energy can emerge from a fiber in the periphery of the cylinder of the catheter to the obstruction. By using laser energy in this way, the periphery of the catheter must be fitted with abutments on the exterior of the catheter periphery, which prevent laser energy from being transmitted outside the abutments. The abutments also encompass the obstruction so that once the obstruction is ablated, it can be suctioned back to the proximal end of the catheter. Since the device must first pass the obstruction, the device is limited to subtotal obstructions which cover a small enough area of the vessel to allow passage of the device. Proper positioning of this device also requires expansion of a balloon to make sure that the abutments are properly placed.

This known art does not disclose how to deliver a beam of energy which is large enough to ablate a large percentage of an obstruction which is in a narrow vessel. An optical fiber with a larger diameter does not have the flexibility required to pass through turns of the vessels. Optical fibers with a small diameter that can be used with a guide wire have only been able to clear obstructions directly in front of the tip of the optical fiber. The present invention overcomes these difficulties to provide for clearing a much greater percentage of the obstruction that is in the vessel.

SUMMARY OF THE INVENTION

The present invention provides for an assembly which uses an optical fiber and guide wire assembled so that the rotation of the catheter causes the emitted laser energy to clear a path which is of a greater diameter than the diameter of the fiber itself. This is accomplished by locating the optical fiber eccentric to the center of the catheter. Rotation of the catheter causes the emitted energy to clear a path of greater diameter than the diameter of the fiber. This catheter assembly can then be used in narrow vessels, such as arteries, to ablate obstructions.

BRIEF DESCRIPTION OF THE DRAWINGS

These and other objects and advantages of this invention will become more apparent and more readily appreciated from the following detailed description of the presently preferred exemplary embodiment, taken in conjunction with the accompanying drawings, of which.

DETAILED DESCRIPTION OF THE PREFERRED EMBODIMENT

Figure 1:
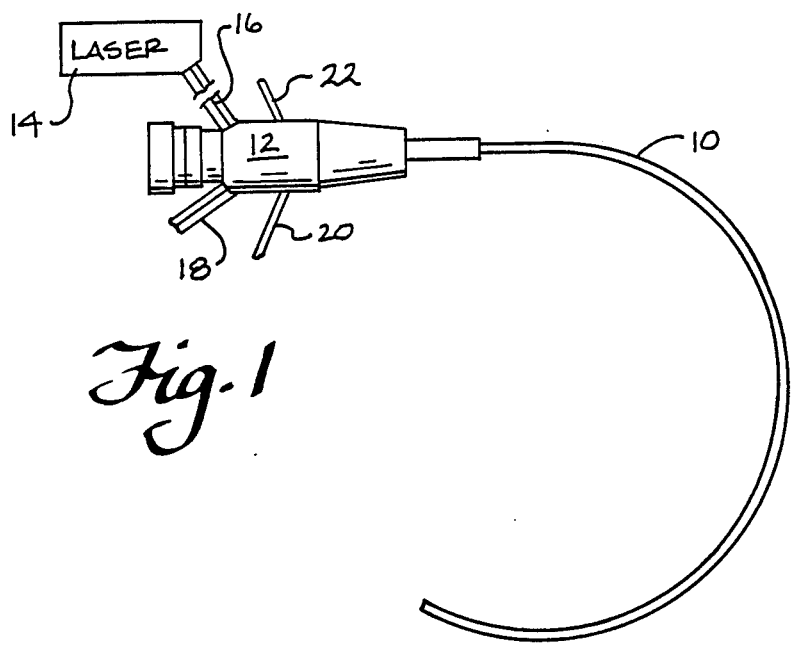
FIG. 1 is an illustration of the complete catheter assembly.

FIG. 1 illustrates the complete catheter assembly of the present invention. Catheter 10 should be made of radiopaque material so that the catheter can be monitored using fluoroscopy as it is advanced to the vessel obstruction. Catheter 10 has a proximal end which is connected to an input device 12. Input device 12 permits the proper connection of laser 14 to optical fiber 16, the proper position required for steering guide wire 18, and the infusion of saline solutions employing tube 20 and contrast dyes employing tube 22, into catheter 10.

Figure 2:
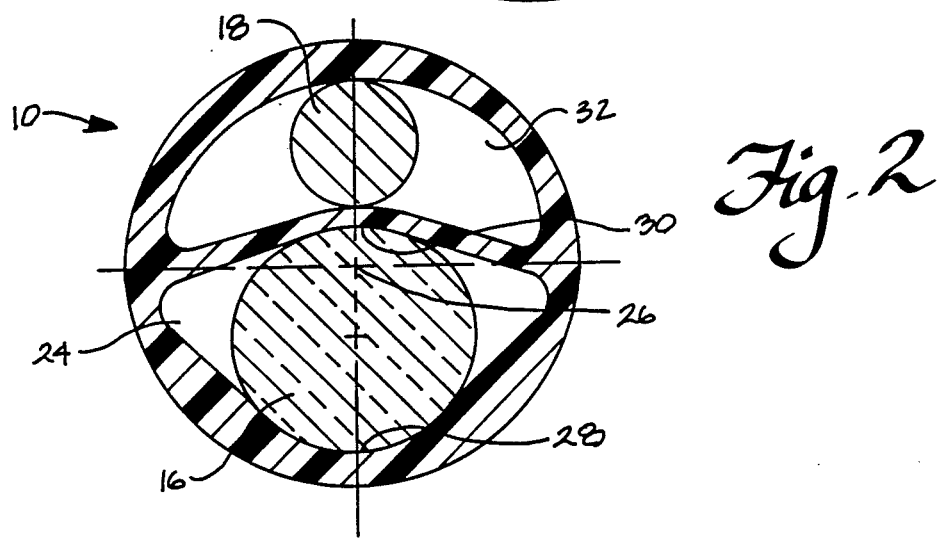
FIG. 2 is a cross section of the catheter.

FIG. 2 shows a cross section of catheter 10. This cross section shows that catheter 10 possesses an eccentric lumen 24 which covers the center 26 of catheter 10.

Optical fiber 16 passes through eccentric lumen 24 and is bonded to the inside wall of eccentric lumen 24 at points 28 and 30 so that fiber 16 covers the center of the catheter. The bonding of the fiber to the catheter does provide some rigidity to the catheter. This helps in allowing the rotation of catheter 10, a subject to be discussed shortly.

Figure 4:
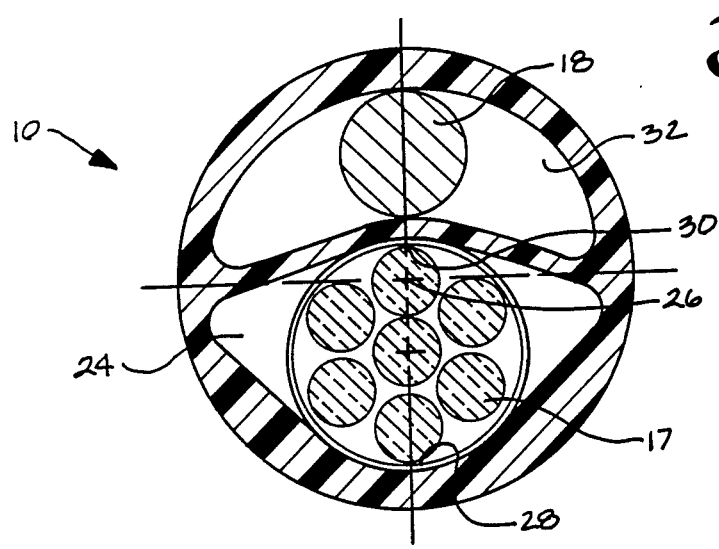
FIG. 4 is a cross section of one embodiment of the catheter using a fiber bundle.

It should be noted that optical fiber 16 can be made from a single fiber as expressly illustrated in FIG. 2, or from a fiber bundle 17 composed of several fibers as illustrated in FIG. 4. The only requisite is that the fiber or fiber bundle must have a small enough diameter to maintain the flexibility necessary to be manipulated through the vessel.

Eccentric lumen 24 is also large enough to allow for the infusion of saline solution or other solutions through the portion of eccentric lumen 24 not displaced by optical fiber 16.

Lumen 32, also within catheter 10, houses steerable guide wire 18. Guide wire 18 allows for catheter 10 to be manipulated to the obstruction within the vessel. Lumen 32 is also used for the infusion of contrast dyes or other solutions.

Figure 3:
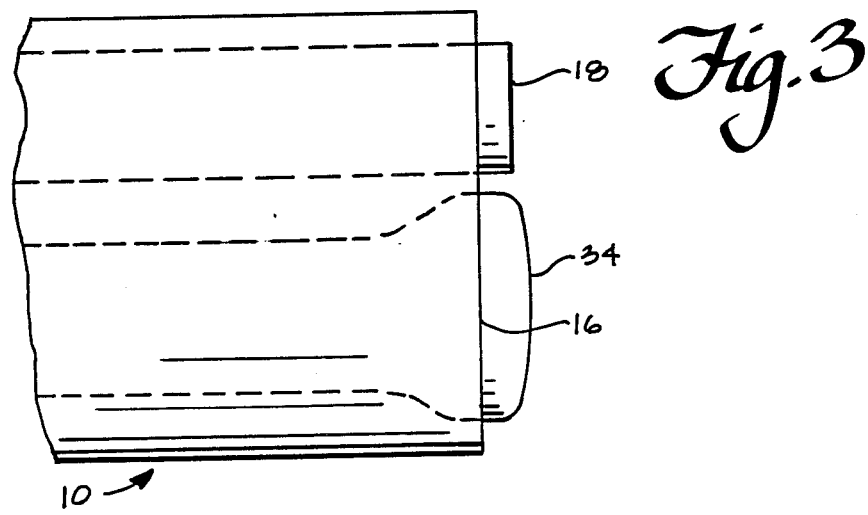
FIG. 3 is an enlarged view of the distal end of the catheter assembly.

FIG. 3 discloses the distal end of catheter 10. It is shown that guide wire 18 and optical fiber 16, although housed in separate lumens, are parallel. Also shown is that the distal end of optical fiber 16 is evenly aligned as close to the distal end of the catheter as possible. This alignment helps reduce perforations to the vessel wall. Perforation of the vessel wall is a problem that has plagued previous optical catheter assemblies.

FIG. 3 also shows that fiber 16 has a bulb-shaped distal end 15. This shape helps reduce the possibility of perforation of the vessel wall. The bulb-shaped distal end is actually part of the fiber itself, and therefore does not require coupling of a separate tip to the fiber. Coupling of a separate tip to a fiber causes an increased energy loss which further reduces the energy available to ablate the obstruction.

Operation of catheter 10 disclosed above takes place as follows. Once the vessel with the obstruction is located, catheter 10, including optical fiber 16 which is bonded to catheter 10, is advanced to the obstruction using guide wire 18 to steer catheter 10 to the correct position. Fluoroscopy is used to see where catheter 10 is actually positioned. During this advancement process, contrast dye may be injected using lumen 32, and laser 14 is turned off.

Once catheter 10 advances to the point of the obstruction, laser 14 is turned on. The energy from laser 14 travels through fiber 16 and is emitted from distal end 34 of fiber 16. The energy supplied is sufficient to ablate the obstruction and recanalize the vessel. Only the portion of the obstruction which makes contact with laser energy is actually ablated. Therefore, rotation of catheter assembly 10 causes fiber 16 to ablate a path which is of a greater diameter than the diameter of fiber 16. The eccentric location of fiber 16 which also covers the center of the catheter ensures that the center of the vessel receives energy from laser 14 and that any obstruction at the center is ablated.

During the time laser 14 is turned on, saline solution can also be infused along tube 20 to keep debris from collecting on the fiber bulb.

As previously mentioned, this arrangement of the fiber and the guide wire within the catheter allows for the fiber to be of a small enough diameter so that the narrow vessels can be cleared of obstructions more fully than previously.

Although only a single preferred embodiment of this invention has been described in detail above, those skilled in the art will readily appreciate that many modifications are possible in the preferred embodiment without materially departing from the novel teachings and advantages of this invention. Accordingly, all such modifications are intended to be included in the scope of this invention as defined by the following claims.

What is claimed is:

1. A catheter assembly comprising:
   a catheter defining a first, eccentric lumen which encompasses the center of the catheter and a second lumen; and
   an optical fiber which runs through said eccentric lumen of said catheter and has a distal end that is eccentric to and encompasses the center of said catheter.

2. A catheter of claim 1 further comprising means for infusing solutions through said eccentric lumen and said second lumen.

3. A catheter of claim 1 wherein said optical fiber is a bundle of fibers.

4. A catheter of claim 1 wherein said catheter is of radiopaque material and said optical fiber has a bulb-tipped distal end.

5. A catheter of claim 1 further comprising a guide wire running through said second lumen.

6. A catheter according to claim 4 wherein said distal end of said optical fiber is substantially aligned with a distal end of said catheter.

7. A catheter of claim 1 in which said optical fiber is bonded to said catheter.

8. An obstruction removal assembly comprising:
   a laser for providing energy sufficient to ablate an obstruction:
   a catheter defining a first, eccentric lumen which encompasses the center of the catheter and a second lumen;
   an optical fiber which runs through said eccentric lumen and has a distal end that is eccentric to and encompasses the center of said catheter; and
   means for coupling energy from said laser to a proximal end of said optical fiber so that said laser energy is emitted from said distal end and ablates said obstruction.

9. An assembly of claim 8 further including a guide wire which runs through said second lumen.

10. An assembly of claim 8 further comprising means for infusing solutions through said eccentric lumen and said second lumen.

11. An assembly of claim 8 wherein said optical fiber is a bundle of fibers.

12. An assembly of claim 8 wherein said catheter is of radiopaque material and said optical fiber has a bulb-tipped distal end.

13. A method for ablating an obstruction in a vessel comprising the steps of:
   positioning a catheter which defines a first eccentric lumen which encompasses the center of the catheter adjacent an obstruction in a vessel; and
   sending energy from a laser through an optical fiber which runs through said eccentric lumen; and emitting said laser energy at a distal end of said optical fiber to irradiate said obstruction; and rotating said catheter, thereby causing said optical fiber to rotate and ablate an area of said obstruction which is of a greater diameter than the diameter of said optical fiber and includes the center of said catheter.

14. A method for ablating an obstruction in a vessel comprising the steps of:

positioning a catheter which defines a first eccentric lumen which encompasses the center of the catheter adjacent an obstruction in a vessel using a guide wire which runs through a second lumen of said catheter;

sending energy from a laser through an optical fiber which runs through said eccentric lumen and has a distal end which is substantially aligned with a distal end of said catheter;

emitting said laser energy from said distal end of optical fiber to irradiate said obstruction; and rotating said catheter, thereby causing said optical fiber to rotate and ablate an area of said obstruction which is of a greater diameter than the diameter of said optical fiber and includes the center of said catheter.

* * * * *